US012734205B2

(12) United States Patent
Choi et al.

(10) Patent No.: US 12,734,205 B2
(45) Date of Patent: Sep. 15, 2026

(54) **COMPLEX COMPOSITION FOR PREVENTING OR TREATING HEARING LOSS INCLUDING SARPOGRELATE AND *VACCINIUM MYRTILLUS* EXTRACT AS ACTIVE INGREDIENTS**

(71) Applicant: IMDpharm Inc., Suwon-si (KR)

(72) Inventors: Sook Choi, Seoul (KR); Sang Kyu Shin, Suwon-si (KR)

(73) Assignee: IMDpharm Inc., Suwon-si (KR)

( * ) Notice: Subject to any disclaimer, the term of this patent is extended or adjusted under 35 U.S.C. 154(b) by 393 days.

(21) Appl. No.: 18/282,790

(22) PCT Filed: Mar. 11, 2022

(86) PCT No.: PCT/KR2022/003423

§ 371 (c)(1),
(2) Date: Sep. 19, 2023

(87) PCT Pub. No.: WO2022/203251

PCT Pub. Date: Sep. 29, 2022

(65) Prior Publication Data

US 2024/0173372 A1 May 30, 2024

(30) Foreign Application Priority Data

Mar. 26, 2021 (KR) ........................ 10-2021-0039541

(51) Int. Cl.
*A61K 36/45* (2006.01)
*A61K 9/00* (2006.01)
*A61K 31/225* (2006.01)
*A61P 27/16* (2006.01)

(52) U.S. Cl.
CPC ............ *A61K 36/45* (2013.01); *A61K 9/0056* (2013.01); *A61K 31/225* (2013.01); *A61P 27/16* (2018.01)

(58) Field of Classification Search
CPC .... A61K 36/45; A61K 9/0056; A61K 31/225; A61K 2236/33; A61K 31/216; A61P 27/16; A23L 33/10; A23L 33/105
See application file for complete search history.

(56) References Cited

U.S. PATENT DOCUMENTS

2020/0121629 A1* 4/2020 Choung ............... A61K 31/216

FOREIGN PATENT DOCUMENTS

| | | | |
|---|---|---|---|
| CN | 106715455 | A | 5/2017 |
| CN | 107929739 | A | 4/2018 |
| JP | 2011-037738 | A | 2/2011 |
| KR | 10-2006-0087846 | | 8/2006 |
| KR | 10-1184725 | B1 | 9/2012 |
| KR | 10-2018-0089207 | A | 8/2018 |
| KR | 10-1905865 | B1 | 10/2018 |
| KR | 10-2019-0071883 | | 6/2019 |
| KR | 10-2019-0073112 | A | 6/2019 |
| KR | 10-2175201 | B1 | 11/2020 |
| KR | 10-2323400 | B1 | 11/2021 |
| WO | 2018/190608 | A1 | 10/2018 |

OTHER PUBLICATIONS

Kapusuz Z, et al. Protective role of bilberry extract against Cisplatin induced ototoxicity in rats. Indian J Otolaryngol Head Neck Surg. Dec. 2013;65(4):339-44, 6 pages. doi: 10.1007/s12070-013-0642-x. Epub Mar. 20, 2013. PMID: 24427595; PMCID: PMC3851505. (Year: 2013).*

International Search Report for PCT/KR2022/003423 mailed Jun. 24, 2022 from Korean Intellectual Property Office.

Kapusuz, Zeliha et al., “Protective role of bilberry extract against cisplatin induced ototoxicity in rats”, Indian Journal of Otolaryngology and Head and Neck Surgery, Mar. 20, 2013 (online publication date), vol. 65, No. 4, pp. 339-344.

Cho, Chang Gun et al., “Evaluation of anxiety and depressive levels in tinnitus patients”, Korean Journal of Audiology, Sep. 24, 2013 (online publication date), vol. 17, No. 2, pp. 83-89.

Sheila A Doggrell, “Sarpogrelate: cardiovascular and renal clinical potential”, Expert Opinion on Investigational Drugs, vol. 13, 2004, Issue 7, pp. 865-874.

* cited by examiner

*Primary Examiner* — Aaron J Kosar
*Assistant Examiner* — Jennifer Lynn Cain
(74) *Attorney, Agent, or Firm* — Revolution IP, PLLC

(57) ABSTRACT

The present invention relates to a complex composition for preventing or treating hearing loss, including sarpogrelate and a *Vaccinium myrtillus* extract as active ingredients, wherein the complex composition has been confirmed to effectively inhibit hair cell death by reactive oxygen species generated by hydrogen peroxide, in a small dose, and exhibit an excellent protective effect on zebrafish auditory hair cells, and therefore, the complex composition can be effectively used as a drug or health food for preventing or treating hearing loss.

4 Claims, 2 Drawing Sheets

[FIG. 1]
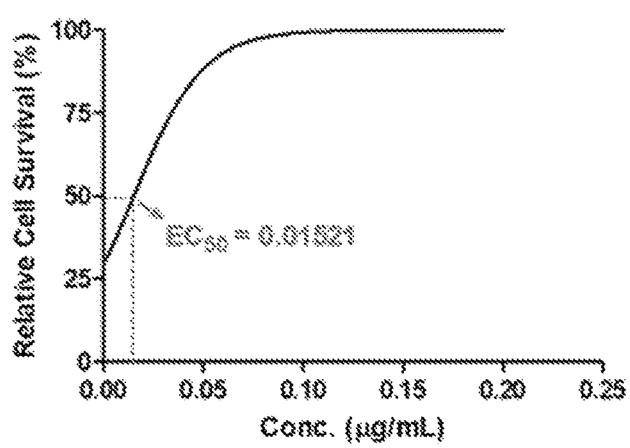
[FIG. 2]
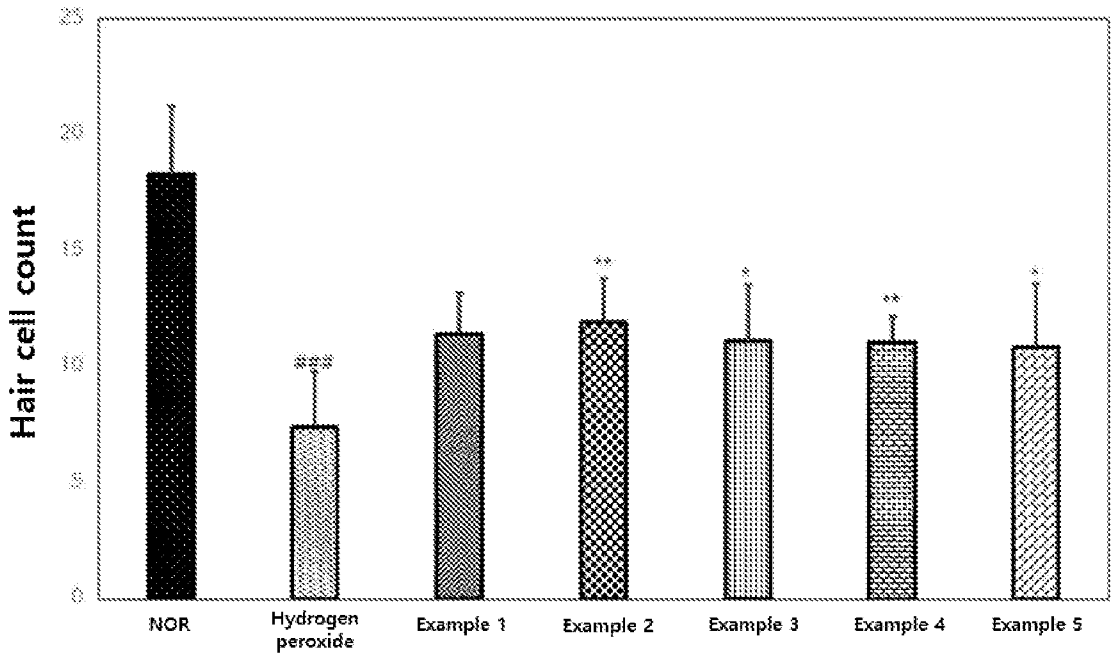

[FIG. 3]
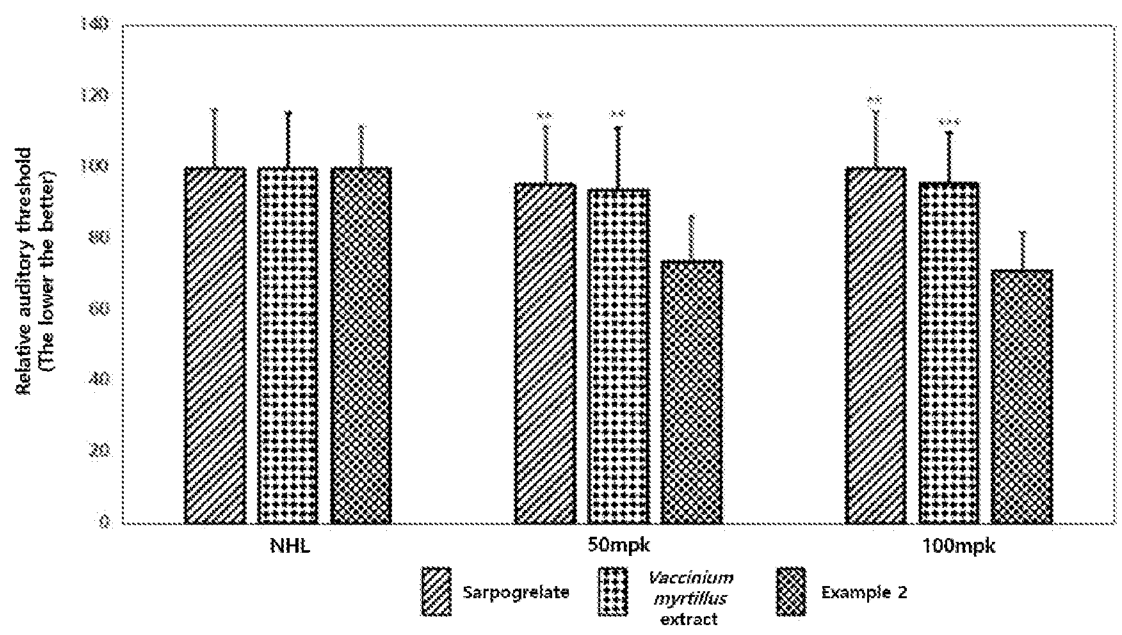

COMPLEX COMPOSITION FOR PREVENTING OR TREATING HEARING LOSS INCLUDING SARPOGRELATE AND *VACCINIUM MYRTILLUS* EXTRACT AS ACTIVE INGREDIENTS

CROSS REFERENCE TO PRIOR APPLICATIONS

This application is a National Stage Application of PCT International Patent Application No. PCT/KR2022/003423 filed on Mar. 11, 2022, under 35 U.S.C. § 371, which claims priority to Korean Patent Application No. 10-2021-0039541 filed Mar. 26, 2021, respectively, which are all hereby incorporated by reference in their entirety.

TECHNICAL FIELD

The present disclosure relates to a composition, for preventing or treating hearing loss, of a complex preparation including sarpogrelate and a *Vaccinium myrtillus* extract as active ingredients.

BACKGROUND ART

Hearing loss, or bradyecoia, is a common disorder that affects about 15-20% of the population, but it has a significant impact on quality of life. In recent years, due to the aging and the spread of digital devices, the number of people with hearing loss is rapidly, gradually increasing, and it is very important to prevent hearing loss before the onset because it is permanent, and fundamental treatment is difficult.

The ear is divided into the outer ear (the eardrum to the earflap), the middle ear (the eardrum to the cochlea), and the inner ear (inside the cochlea), and the hearing loss caused by disorders in the outer ear and the middle ear is ameliorated once the disorder is treated, but it is hard to recover from hearing loss that is caused by disorders in the inner ear and the auditory nervous system even if it is treated.

Hearing loss may be divided into presbyacusia, pediatric hearing loss, Ménière's disease, sudden hearing loss, noise induced hearing loss, and ototoxic hearing loss, among which the most common forms are noise induced hearing loss and ototoxic hearing loss attributable to noise and drugs, while noise induced hearing loss is increasing drastically in recent years.

The human auditory organ is affected at noise levels above 75 dBA, which is equivalent to living in an industrial society where everyone is under the influence of noise that is harmful to the auditory organ. Moreover, frequent exposure of the auditory organ to loud sounds due to the use of earphones increases the number of patients suffering from noise induced hearing loss in various age groups. Noise induced hearing loss in young ages would become more severe with age, affecting people in all ages.

Further, ototoxic hearing loss is known to occur by apoptosis due to active oxygen generated by ototoxic drugs.

Although antioxidants have been used predominantly for studies conducted for prevention and treatment of noise induced hearing loss and ototoxic hearing loss, there are no drugs that show a distinctive preventive effect, and the safety of many drugs has not been proven so far.

DISCLOSURE OF THE INVENTION

Technical Goals

An object of the present disclosure is to provide a composition, including sarpogrelate and a *Vaccinium myrtillus* extract as active ingredients, as a pharmaceutical composition and health food for preventing or treating hearing loss caused by reactive oxygen species generated by noise or drug exposure.

Technical Solutions

The present disclosure provides a pharmaceutical composition for preventing or treating hearing loss including sarpogrelate and a *Vaccinium myrtillus* extract as active ingredients.

In addition, the present disclosure provides a health food for preventing or ameliorating hearing loss including sarpogrelate and a *Vaccinium myrtillus* extract as active ingredients.

Advantageous Effects

According to the present disclosure, it was found that a composition including a complex composition in which sarpogrelate and a *Vaccinium myrtillus* extract are mixed at a weight ratio of 1:(0.125 to 8) as active ingredients effectively inhibits hair cell death caused by reactive oxygen species generated by hydrogen peroxide at a small dose and exhibits an excellent protective effect on zebrafish auditory hair cells, such that it is possible to provide the composition, including sarpogrelate and a *Vaccinium myrtillus* extract as active ingredients, as a composition for preventing or treating sensorineural hearing loss.

BRIEF DESCRIPTION OF DRAWINGS

FIG. 1 shows a result of determining an $EC_{50}$ value for hair cells obtained as a test result for an apoptosis inhibitory effect in an auditory cell line.

FIG. 2 shows a result of checking an efficacy test on hair cells in a zebrafish drug efficacy model of a complex composition according to a composition ratio of the present disclosure.

FIG. 3 shows a result of a comparative test for hearing improvement efficacy of sarpogrelate, a *Vaccinium myrtillus* extract, and a composite composition of the present disclosure in an in vivo mouse model with noise induced hearing loss.

BEST MODE FOR CARRYING OUT THE INVENTION

Hereinafter, the present disclosure will be described in more detail.

As noise and ototoxic drugs generate active oxygen, and the active oxygen thus generated induces apoptosis of auditory cells to cause noise induced hearing loss and ototoxic hearing loss, the inventors of the present disclosure completed the present disclosure by finding, in the course of conducting a research for a therapeutic agent for more effectively treating hearing loss caused by active oxygen, that a complex composition including sarpogrelate and a *Vaccinium myrtillus* extract as active ingredients in an optimal weight ratio exhibits an excellent protective effect on auditory cells exposed to active oxygen even with a small dose.

The present disclosure may provide a pharmaceutical composition for preventing or treating hearing loss including sarpogrelate and a *Vaccinium myrtillus* extract as active ingredients.

More specifically, the hearing loss may be selected from the group consisting of noise induced hearing loss, ototoxic hearing loss, presbyacusia, and sudden hearing loss, and as an example, the hearing loss may be noise induced hearing loss or ototoxic hearing loss induced by hydrogen peroxide or reactive oxygen species (ROS).

The pharmaceutical composition may be a complex composition consisting of sarpogrelate and a *Vaccinium myrtillus* extract at a weight ratio of 1:(0.125 to 8). Preferably, it may be a complex composition having a weight ratio of 1:2 to 4 for sarpogrelate to the *Vaccinium myrtillus* extract, and more preferably a complex composition having a weight ratio of 1:3 for sarpogrelate to the *Vaccinium myrtillus* extract.

The complex composition may exhibit an elevated auditory ameliorating effect that is higher than a simple increasing effect of a product value of an efficacy of a substance consisting of single components which are sarpogrelate or the *Vaccinium myrtillus* extract. When the weight ratio of sarpogrelate and the *Vaccinium myrtillus* extract is less than 1:0.125, it is difficult to expect a synergistic effect as a complex composition due to low content of *Vaccinium myrtillus* that may be compounded with respect to 300 mg of sarpogrelate that is a recommended daily dose, and even if the weight ratio of sarpogrelate and the *Vaccinium myrtillus* extract is greater than 1:8, it is still difficult to expect a synergistic effect as a complex composition due to low content of sarpogrelate that is compounded with respect to 510 mg that is a recommended daily dose of *Vaccinium myrtillus*.

The *Vaccinium myrtillus* extract used in the present disclosure is an extract of *Vaccinium myrtillus* fruit/leaf parts using water, C1 to C4 alcohol, or a solvent mixture thereof as an extraction solvent, and a method of preparing an extract includes performing extraction with solid powder of *Vaccinium myrtillus* fruit/leaf parts using 5 to 30 times the extraction solvent via a cold precipitation method, warm precipitation method, and percolation method, concentrating the extract, and then processing into powder by undergoing spray-drying or freeze-drying with addition of a form a soft extract, a soft extract alone, or a soft extract along with excipients such as dextran.

Sarpogrelate, one of components of the present disclosure, is (−)-4-[1-dimethylamino-3-[2-[2-(3-methoxyphenyl) ethyl]phenoxy]propan-2-yl]oxy-4-oxobutanoic acid, which is a drug having a molecular structure represented by $C_{24}H_{31}NO_6$ with the following structure and generally in the form of hydrochloride. Sarpogrelate, a component of the present disclosure, is not limited to hydrochloride and may include any salt, including free bases or hydrochloride.

[Chemical formula]

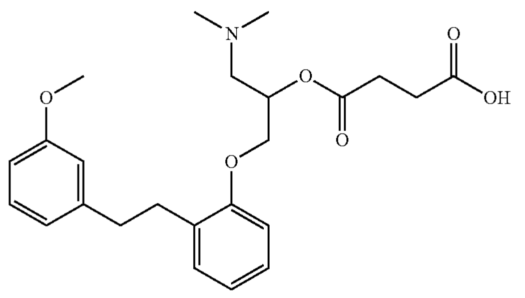

The pharmaceutical composition may inhibit apoptosis of auditory cells and increase the number of hair cells.

According to an example embodiment of the present disclosure, it was observed that the complex extract, compared to single administration of the *Vaccinium myrtillus* extract, showed inhibition of apoptosis of auditory cell lines by up to 21.5% at the same concentration, and further increased an efficacy by up to 22% in the comparison of the number of hair cells in zebrafish with single administration of sarpogrelate.

In particular, it was found that Example 2 in which sarpogrelate and the *Vaccinium myrtillus* extract are mixed at a weight ratio of 1:3 showed, in an auditory brainstem response test in mice for 14 days, 21.6% p and 28.8% p higher effects than sarpogrelate at a dose of 50 mpk and 100 mpk under a click sound condition as well as 19.9% p and 24.5% p higher threshold improvement effect than the *Vaccinium myrtillus* extract at the same dose, respectively.

In an example embodiment of the present disclosure, the pharmaceutical composition for preventing or treating hearing loss including sarpogrelate and a *Vaccinium myrtillus* extract as active ingredients may use any one formulation selected from the group consisting of injections, granules, powder, tablets, pills, capsules, suppositories, gels, suspensions, emulsions, drops, or liquids according to a conventional method.

In another example embodiment of the present disclosure, the pharmaceutical composition may further include one or more appropriate additives selected from the group consisting of carriers, excipients, disintegrants, sweeteners, coating agents, swelling agents, lubricants, flavoring agents, antioxidants, buffers, bacteriostatic agents, diluents, dispersants, surfactants, binders, and antifriction agents that are commonly used in the preparation of pharmaceutical compositions.

Specifically, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil may be used as carriers, excipients, and diluents, and solid preparations for oral administration include tablets, pills, powder, granules and capsules, wherein such solid preparation may be prepared by mixing the composition with at least one excipient such as starch, calcium carbonate, sucrose or lactose, and gelatin. In addition to simple excipients, lubricants such as magnesium stearate and talc may also be used. Liquid preparations for oral use include suspensions, solutions, emulsions, and syrups, and various excipients such as wetting agents, sweeteners, fragrances, and preservatives may be included in addition to commonly used simple diluents such as water and liquid paraffin. Preparations for parenteral administration include sterile aqueous solutions, non-aqueous solutions, suspensions, emulsions, freeze-dried preparations, and suppositories. Propylene glycol, polyethylene glycol, vegetable oils such as olive oil, and injectable esters such as ethyl oleate may be used as non-aqueous solvents and suspending agents. Witepsol, macrogol, Tween 61, cacao butter, laurin fat, and glycerogelatin may be used as a base of the suppositories.

According to an example embodiment of the present disclosure, the pharmaceutical composition is administered to a subject in a conventional manner via intravenous, intraarterial, intraperitoneal, intramuscular, intrasternal, transdermal, intranasal, inhalational, topical, rectal, oral, intraocular, or intradermal routes.

Preferred dosages of the composition including sarpogrelate and the *Vaccinium myrtillus* extract as active ingredients may vary depending on the subject's condition and weight, the type and extent of a disease, drug form, the route and duration of administration, and may be appropriately selected by those skilled in the art. According to an example embodiment of the present disclosure, although not limited thereto, the daily dose may be 0.01 to 200 mg/kg, specifically 0.1 to 200 mg/kg, and more specifically 0.1 to 100 mg/kg. Administration may be conducted once a day or in several divided doses, thereby not limiting the scope of the present disclosure.

In an example embodiment of the present disclosure, the term 'subject' as used herein may refer to a mammal including a human but is not limited to the examples.

In addition, the present disclosure may provide a health food for preventing or ameliorating hearing loss including sarpogrelate and a *Vaccinium myrtillus* extract as active ingredients.

The health food may be used with other foods or food additives other than the sarpogrelate and *Vaccinium myrtillus* extract and may be used appropriately according to conventional methods. The mixed amount of the active ingredient may be suitably determined depending on the purpose of use thereof, for example, prevention, health, or therapeutic treatment.

The effective dose of a compound included in the health food may be used in accordance with the effective dose of the therapeutic agent, but in the case of long-term intake for health and hygiene or health control, it should be less than or equal to the above range, and it is certain that the active ingredient may be used in an amount beyond the above range since there is no problem in terms of safety.

The type of health food is not particularly limited, and examples may include meat, sausage, bread, chocolate, candy, snacks, confectionery, pizza, ramen, other noodles, gum, dairy products including ice cream, various soups, beverages, tea, drinks, alcoholic beverages, and vitamin complexes.

MODES FOR CARRYING OUT THE INVENTION

Hereinafter, example embodiments will be described in detail to help the understanding of the present disclosure. However, the following example embodiments are merely illustrative of the content of the present disclosure, and the scope of the present disclosure is not limited to the following example embodiments. The example embodiments of the present disclosure are provided to more completely explain the present disclosure to those skilled in the art.

<Examples 1 to 5> Preparation of Complex Composition of *Vaccinium myrtillus* Ethanol Extract and Sarpogrelate A *Vaccinium myrtillus* extract was primarily extracted by adding 100 g of *Vaccinium myrtillus* to 1 L of 90 (v/v) % aqueous ethanol solution and then stirring at 40° C. and 1600 rpm for 2 hours. The extract solution of the primary extract was transferred, 1 L of 70 (v/v) % aqueous ethanol solution was added to the residue, and then stirring was performed at 40° C. and 1600 rpm for 2 hours to perform the secondary extraction, followed by transfer of the secondary extract solution. Thereafter, 1 L of 70 (v/v) % aqueous ethanol solution was added to the secondary residue, and the mixture was tertiarily extracted in the same way.

After mixing the primary, secondary, and tertiary extract solutions, alcohol was evaporated while concentrating at a temperature below 50° C. The concentrate obtained by the above process was diluted to 1.5±5% Brix and centrifuged at 6900 rpm for 6 to 12 minutes.

The supernatant obtained by centrifugation was press-filtered and purified. Thereafter, 1200 L of water was added to the purified solution for primary washing for 2 hours, 5000 L of 70 (v/v) % ethanol was added to the primarily washed purified solution for the secondary washing, and the washing solution was collected and concentrated.

The concentrate obtained by the above process was spray-dried to prepare a powdered *Vaccinium myrtillus* ethanol extract.

The powdered *Vaccinium myrtillus* ethanol extract was added with sarpogrelate hydrochloride (manufacturer: Pharmacostech) in a weight ratio shown in Table 1, and a *Vaccinium myrtillus* extract and sarpogrelate were put into a mixer and mixed at a rate of 50 rpm for 5 minutes to prepare a complex composition.

TABLE 1

| | Example 1 | Example 2 | Example 3 | Example 4 | Example 5 |
|---|---|---|---|---|---|
| *Vaccinium myrtillus* ethanol extract | 10 g | 30 g | 80 g | 10 g | 10 g |
| Sarpogrelate | 10 g | 10 g | 10 g | 30 g | 80 g |
| Weight of complex composition | 20 g | 40 g | 90 g | 40 g | 90 g |

<Examples 6 to 10> Preparation of Complex Composition of *Vaccinium myrtillus* Ethanol Extract and Sarpogrelate 100 g of *Vaccinium myrtillus* was added to 0.5 L of 70 (v/v) % aqueous ethanol solution, and stirring was performed at 60° C. and 1600 rpm for 2 hours for primary extraction. The extract solution of primary extract was transferred, 0.5 L of 70 (v/v) % aqueous ethanol solution was added to the residue, and then stirring was performed at 60° C. and 1600 rpm for 2 hours for secondary extraction, followed by transfer of the secondary extract solution. Thereafter, 0.5 L of 70 (v/v) % aqueous ethanol solution was added to the secondary residue, and the mixture was tertiarily extracted in the same way.

After mixing the primary, secondary, and tertiary extract solutions, alcohol was evaporated while concentrating at a temperature below 50° C. The concentrate obtained by the above process was diluted to 3±5% Brix and centrifuged at 6900 rpm for 6 to 12 minutes.

The supernatant obtained by centrifugation was press-filtered and purified. Thereafter, 1200 L of water was added to the purified solution for primary washing for 2 hours, 5000 L of 70 (v/v) % ethanol was added to the primarily washed purified solution for the secondary washing, and the washing solution was collected and concentrated. The concentrate obtained thereby was lyophilized to prepare a powdered *Vaccinium myrtillus* ethanol extract.

The powdered *Vaccinium myrtillus* ethanol extract was added with sarpogrelate hydrochloride (manufacturer: Pharmacostech) in a weight ratio shown in Table 2, and a *Vaccinium myrtillus* extract and sarpogrelate were put into a mixer and mixed at a rate of 50 rpm for 5 minutes to prepare a complex composition.

TABLE 2

| | Example 6 | Example 7 | Example 8 | Example 9 | Example 10 |
|---|---|---|---|---|---|
| *Vaccinium myrtillus* ethanol extract | 10 g | 30 g | 40 g | 10 g | 10 g |
| Sarpogrelate | 10 g | 10 g | 10 g | 20 g | 50 g |
| Weight of complex composition | 20 g | 40 g | 50 g | 30 g | 60 g |

<Examples 11 to 13> Preparation of Complex Composition of *Vaccinium myrtillus* Methanol Extract and Sarpogrelate The *Vaccinium myrtillus* methanol extract was prepared by pulverizing frozen *Vaccinium myrtillus* pulp, immersing 100 g of the pulverized substance in 0.5 to 1 L of 70 (v/v) % aqueous methanol solution, and then performing extraction at 28 to 30° C. Thereafter, the supernatant was separated by centrifugation, citric acid was added to the separated supernatant, and the resulting precipitate was removed for purification. Thereafter, the remaining extract solution was concentrated, diluted by adding ethanol, and dried at 60° C. for 36 hours to prepare dry powder.

The *Vaccinium myrtillus* methanol extract obtained by the above process was added with sarpogrelate hydrochloride (manufacturer: Pharmacostech) in a weight ratio shown in Table 3, and a *Vaccinium myrtillus* extract and sarpogrelate were put into a mixer and mixed at a rate of 50 rpm for 5 minutes to prepare a complex composition.

TABLE 3

| | Example 11 | Example 12 | Example 13 |
|---|---|---|---|
| *Vaccinium myrtillus* methanol extract | 10 g | 30 g | 50 g |
| Sarpogrelate | 10 g | 10 g | 10 g |
| Weight of complex composition | 20 g | 40 g | 50 g |

<Examples 14 to 15> Preparation of Complex Composition of *Vaccinium myrtillus* Methanol Extract and Sarpogrelate 100 g of *Vaccinium myrtillus* was added to 1 L of 70 (v/v) % aqueous methanol solution, and stirring was performed at 30° C. and 1600 rpm for 2 hours for primary extraction. The extract solution of the primary extract was transferred, 1 L of 70 (v/v) % aqueous methanol solution was added to the residue, and then stirring was performed at 30° C. and 1600 rpm for 2 hours for secondary extraction, followed by transfer of the secondary extract solution. Thereafter, 1 L of 70 (v/v) % aqueous methanol solution was added to the secondary residue, and the mixture was tertiarily extracted in the same way.

After mixing the primary, secondary, and tertiary extract solutions, alcohol was evaporated while concentrating at a temperature below 50° C. The concentrate obtained by the above process was diluted to 3±5% Brix and centrifuged at 6900 rpm for 6 to 12 minutes.

The supernatant obtained by centrifugation was press-filtered and purified. Thereafter, 1200 L of water was added to the purified solution for primary washing for 2 hours, 5000 L of 70 (v/v) % methanol was added to the primarily washed purified solution for the secondary washing, and the washing solution was collected and concentrated. The concentrate obtained thereby was spray-dried to prepare a powdered *Vaccinium myrtillus* methanol extract.

The *Vaccinium myrtillus* methanol extract obtained thereby was added with sarpogrelate hydrochloride (manufacturer: Pharmacostech) in a weight ratio shown in Table 4, and a *Vaccinium myrtillus* extract and sarpogrelate were put into a mixer and mixed at a rate of 50 rpm for 5 minutes to prepare a complex composition.

TABLE 4

| | Example 14 | Example 15 |
|---|---|---|
| *Vaccinium myrtillus* methanol extract | 30 g | 30 g |
| Sarpogrelate | 30 g | 10 g |
| Weight of complex composition | 60 g | 40 g |

<Examples 16 to 20> Preparation of Complex Composition of *Vaccinium myrtillus* Water Extract and Sarpogrelate A *Vaccinium myrtillus* water extract was obtained by adding 30 g of frozen *Vaccinium myrtillus* pulp to 600 mL of water and performing hot water extraction at 110° C. for 3 hours to obtain a hot water extract which was then concentrated with a vacuum concentrator until a solid content becomes 30%, followed by lyophilization to prepare dry powder.

The *Vaccinium myrtillus* extract obtained by the above process was added with sarpogrelate hydrochloride (manufacturer: Pharmacostech) in a weight ratio shown in Table 5, and a *Vaccinium myrtillus* extract and sarpogrelate were put into a mixer and mixed at a rate of 50 rpm for 5 minutes to prepare a complex composition.

TABLE 5

| | Example 16 | Example 17 | Example 18 | Example 19 | Example 20 |
|---|---|---|---|---|---|
| *Vaccinium myrtillus* water extract | 10 g | 30 g | 80 g | 10 g | 10 g |
| Sarpogrelate | 10 g | 10 g | 10 g | 30 g | 80 g |
| Weight of complex composition | 20 g | 40 g | 90 g | 40 g | 90 g |

<Test Example 1> Identification of an Apoptosis Inhibitory Effect on Auditory Cell Lines by the Complex Composition House Ear Institute-Organ of *Corti* 1 (HEI-OC1), an auditory hair cell derived from the Organ of *Corti* which is the auditory generation organ in mice, was cultured in an incubator at 33° C. in the presence of 10% $CO_2$ using DMEM (high-glucose Dulbecco's Eagle's medium, Sigma-Aldrich Co., St. Louis, USA) culture including 10% fetal bovine serum (FBS; WELGENE Inc., Gyeongsangbuk-do, Korea) and 50 U/mL INF-γ (Peprotech Inc., Seoul, Korea) without addition of antibiotics.

In order to generate reactive oxygen species (ROS) caused by oxidative stress that occurs in the process of inducing noise induced hearing loss, cell lines with noise induced hearing loss were established by treating hydrogen peroxide.

The complex composition in Example 2 was treated to the cell lines induced with noise induced hearing loss at concentrations of 0.001, 0.005, 0.01, 0.05, 0.1, and 0.5 μg/mL for 1 hour, and then treatment of 100 μM hydrogen peroxide was performed for 24 hours to identify the cytotoxic and apoptotic effects by hydrogen peroxide via MTT analysis.

As shown in Table 6 and FIG. 1, the apoptosis inhibitory effect on auditory cells was identified in the complex composition in Example 2. Compared with sarpogrelate, it was found that the auditory cell apoptotic effect was significantly excellent.

TABLE 6

| μg/mL | CTL | $H_2O_2$ | 0.001 | 0.005 | 0.01 | 0.05 | 0.1 | 0.2 |
|---|---|---|---|---|---|---|---|---|
| Relative cell viability | 100 | 0.0 | 53.7 | 60.7 | 77.1 | 89.9 | 97.3 | 93.7 |

As a result, as shown in FIG. 1, the EC50 of the complex composition in Example 2 was found to be 0.015 μg/mL. Additionally checked EC50 of sarpogrelate and the *Vaccinium myrtillus* extract was found to be 26.43 μg/mL and 0.16 μg/mL, respectively, showing higher efficacy than a single preparation.

From the above results, it was determined that the complex composition in Example 2 may exhibit a superior apoptosis inhibitory effect than each single preparation with a small dose.

<Test Example 2> Efficacy Test for Hair Cells in Zebrafish Drug Efficacy Models

Zebrafish have an inner ear structure similar to that of human and is transparent to be easy to observe while the lateral line system, which is an additional auditory organ, is exposed to the outside, such that changes in auditory hair cells after noise exposure or drug administration may be observed in a live organism state, thereby being used as a model organism for reactive oxygen induced hearing loss.

For preparation of zebrafish larvae, females and males were placed in a 1:1 ratio in a tank with a net installed to separate eggs from adults, and zebrafish embryos were collected after 12 hours.

After collection, washing was followed 3 times using 0.03% sea salt solution to remove foreign substances, and breeding was performed in an incubator under a photoperiod (14 light/10 dark) at 28.5° C. After placing zebrafish larvae (6 dpf) in 24-well 6 days after fertilization, 2.5 mM hydrogen peroxide was treated for 3 hours of exposure to prepare a model with hydrogen peroxide induced hearing loss, and an untreated normal control without treatment of hydrogen peroxide was prepared.

Zebrafish models with hydrogen peroxide induced hearing loss were treated at concentrations of 0.1, 0.5, and 1 μg/mL, respectively, from Example 1 to Example 5 for 12 hours of exposure.

Zebrafish larvae that had been tested for toxicity were anesthetized with 0.02% tricaine, auditory hair cells were stained with 0.1% YO-PRO for 30 minutes, and auditory hair cells were observed and counted using fluorescence microscope (Olympus 1×70, Olympus, Japan).

As a result, as shown in FIG. 2, all the groups subjected to treatment from Example 1 to Example 5 showed the effect of inhibiting cytotoxicity by hydrogen peroxide in zebrafish hair cells.

Especially, when the 0.1 μg/mL complex composition in Example 2 was administered as shown in FIG. 3, an average of 12.74 hair cells could be observed, proving that the complex composition in Example 2 had the highest hair cell protective efficacy through the threshold improvement effect of each of the *Vaccinium myrtillus* extract and sarpogrelate.

<Test Example 3> Comparative Test for Hearing Amelioration Efficacy in In Vivo Mouse Models The animals used in the experiment were bred in a lighted environment every 12 hours at a temperature controlled at 25±2° C., and in order to induce noise induced hearing loss, the mice were exposed to a complex sound at 115 dB for 90 minutes to prepare noise induced hearing loss (NIHL) model mice.

To evaluate the efficacy of a sample in NIHL model mice, the auditory threshold was measured using the auditory brainstem response (ABR) measurement.

The NIHL mouse models were orally administered with samples at the same time daily for the complex composition treated group in Example 2 after 20 hours of exposure to noise, while no administration was applied to the control. Measurement was performed for all mice after checking the state of the ear canal through otoscopy before the experiment.

For the stimulus sound, evaluation was performed by gradually lowering the click sound (wide range frequency) by 5 dB from 80 dB, and the 14-day measurement result was applied for the lowest value by setting the smallest sound having responses as a threshold.

As a result, as shown in FIG. 3, the auditory threshold was reduced by up to 30% p, compared to the control that did not receive the drug, in the group treated with sarpogrelate, the *Vaccinium myrtillus* extract, and the complex composition in Example 2, and a statistically significant difference was observed.

Although specific parts of the present disclosure have been described in detail above, it is clear for those skilled in the art that these specific descriptions are merely preferred example embodiments, and the scope of the present disclosure is not limited thereto. Accordingly, the substantial scope of the present disclosure will be defined by the appended claims and equivalents thereof.

The invention claimed is:

1. A method of preventing or treating hearing loss in a subject in need thereof, comprising:

administering a pharmaceutical composition comprising sarpogrelate and a *Vaccinium myrtillus* extract in a weight ratio of 1:2 to 1:8 as active ingredients to the subject, wherein the pharmaceutical composition inhibits apoptosis of auditory cells and increases the number of hair cells, compared to single administration of the *Vaccinium myrtillus* extract or sarpogrelate.

2. The method of claim 1, wherein the *Vaccinium myrtillus* extract is obtained by extraction with water, C1 to C4 alcohol, or a composite solvent thereof.

3. The method of claim 1, wherein the hearing loss is selected from the group consisting of noise induced hearing loss, ototoxic hearing loss, presbyacusia, and sudden hearing loss.

4. A method of preventing or ameliorating hearing loss in a subject in need thereof, comprising:

administering a health food comprising sarpogrelate and a *Vaccinium myrtillus* extract in a weight ratio of 1:2 to 1:8 as active ingredients to the subject, wherein the health food inhibits apoptosis of auditory cells and increases the number of hair cells, compared to single administration of the *Vaccinium myrtillus* extract or sarpogrelate.

* * * * *